United States Patent
Wada et al.

[11] Patent Number: 5,965,150
[45] Date of Patent: Oct. 12, 1999

[54] CAPSULE PREPARATIONS FOR PLANT TREATMENT

[75] Inventors: Yuzuru Wada, Hachioji; Kunihiro Isono, Tochigi; Yuichi Otsu, Oyama; Shinaburo Sone, Yuki; Katsuhiko Hanaki, Tochigi; Takahisa Abe, Oyama, all of Japan

[73] Assignee: Nihon Bayer Agrochem K.K., Tokyo, Japan

[21] Appl. No.: 08/635,046

[22] Filed: Apr. 19, 1996

[30] Foreign Application Priority Data

Apr. 28, 1995 [JP] Japan .................................. 7-127514

[51] Int. Cl.$^6$ .................................................. A01N 25/10
[52] U.S. Cl. .................... 424/408; 424/78.18; 424/78.31
[58] Field of Search .................. 424/408, 78.18, 424/78.31

[56] References Cited

U.S. PATENT DOCUMENTS

| | | |
|---|---|---|
| 1,727,939 | 9/1929 | Renner . |
| 1,756,453 | 4/1930 | Davey et al. . |
| 2,947,111 | 8/1960 | Zobrist . |
| 3,254,449 | 6/1966 | Mauget . |
| 3,304,655 | 2/1967 | Mauget . |
| 3,367,065 | 2/1968 | Cravens . |
| 3,576,276 | 4/1971 | Clarke . |
| 3,608,239 | 9/1971 | Tucker . |
| 3,691,683 | 9/1972 | Sterik . |
| 3,706,161 | 12/1972 | Jenson . |
| 3,832,803 | 9/1974 | Blake et al. . |
| 3,834,075 | 9/1974 | Nix et al. . |
| 3,864,874 | 2/1975 | Norris et al. . |
| 3,920,393 | 11/1975 | Baynes et al. . |
| 3,992,813 | 11/1976 | Freshel . |
| 4,028,846 | 6/1977 | Floyd et al. . |
| 4,144,673 | 3/1979 | Quast et al. . |
| 4,342,176 | 8/1982 | Wolfe . |
| 4,793,474 | 12/1988 | Drake . |
| 4,921,703 | 5/1990 | Higuchi et al. ................. 424/419 |

FOREIGN PATENT DOCUMENTS

| | | |
|---|---|---|
| 4341442 | 6/1995 | Germany . |

*Primary Examiner*—Neil S. Levy
*Attorney, Agent, or Firm*—Sprung Kramer Schaefer & Briscoe

[57] ABSTRACT

Novel capsule preparations for the treatment of plants, which preparations are composed of A) a capsule shell comprising
   water-soluble polyoxyethylene having a number average molecular weight of 100,000 or more,
   at least one plasticizer and
   optionally, one or more additives,
   and
B) a filling comprising
   at least one biologically active compound and
   optionally, one or more auxiliaries, and a method for administering biologically active compounds to plants, such as trees and shrubs, by inserting the novel capsule preparations into the plants.

3 Claims, No Drawings

CAPSULE PREPARATIONS FOR PLANT TREATMENT

The Present invention relates to new capsule preparations and to their use for treating plants.

The method, which has been hitherto mostly employed for administering biologically active compounds to plant bodies, consists in applying the active ingredients in the form of appropriate formulations to the whole plant by means of atomizing, spraying, spreading, etc. This method is suitable either for bringing the active compounds directly into contact with pests which are ectoparasitic on plants, or for allowing the active compounds to penetrate into the plant bodies and then to be transported within the plants to the site of action.

Another method for administering biologically active compounds to plants consists in applying the active ingredients in the form of appropriate formulations to the soil surrounding the plants. The active compounds are absorbed by the roots of the plants and then are transported within the plants to the site of action.

Upon working according to the above-mentioned methods, however, substantial quantities of the active compounds are wasted because they run off by rain water or are drifted away by wind, thus causing a further problem of environmental pollution.

To avoid these disadvantages, several other methods have been proposed for protecting plants, such as trees, from pests. For instance, it has been suggested to inject a solution of a certain insecticide into the stem of deciduous trees or coniferous trees or by embedding a powder preparation therein (see Chem. Abstr. 108, 181 188w; Chem. Abstr. 99, 83 692v; Chem. Abstr. 99, 181 184 and Chem. Abstr. 87, 146 712). However, these methods are only used in the case of applying insecticidally active compounds which have systemic properties and are easily soluble in water.

Furthermore, when said method is carried out under practical working conditions, particularly when the appropriate amounts of active compounds are introduced into the running sap in order to minimize the damage of the plants as far as possible, no adequate effects are achieved. Such method, however, is carried out on a few kinds of plants for experimental purpose.

It has also been disclosed to use a solid treatment agent consisting of an active compound and a polymeric matrix, in which the active compound is embedded (see Chem. Abstr. 100, 47 099n and U.S. Pat. No. 3,269,900). The active compound is gradually released from the matrix to the soil for a relatively long period of time. Furthermore, there are known preparations containing a polymer and an active compound, which preparations are suitable for uniformly releasing an easily volatile active compound into the atmosphere for a relatively long period of time (see U.S. Pat. No. 3,318,764).

Methods for combating pine disease causative *Bursaphelenchus xylonhilus* Nickle, by which increasing damages have been observed recently, are also known. Thus, extensive air-application of insecticides has been conducted to control *Monochamus alternatus* which is a carrier of *Bursaphelenchus xylophilus* Nickle. After all, ampule-injecton of insecticides into stems has been used to combat *Bursaphelenchus xylophilus* Nickle itself. However, the air-application of insecticides may cause a problem of environmental pollution. On the other hand, when combating pests by means of ampule-injection, the ampules must be recovered after the application. Other disadvantages of this method are the inhibition of the water passage in the stem and the destruction of cambium.

There have now been found capsule preparations for the treatment of plants, which preparations are composed of A) a capsule shell comprising
   water-soluble polyoxyethylene having a number average molecular weight of 100,000 or more,
   at least one plasticizer and
   optionally, one or more additives,
   and
B) a filling comprising
   at least one biologically active compound and
   optionally, one or more auxiliaries.

There has also been found a method for administering biologically active compounds to plants, which method consists in inserting into the plants capsule preparations composed of A) a capsule shell comprising
   water-soluble polyoxyethylene having a number average molecular weight of 100,000 or more,
   at least one plasticizer and
   optionally, one or more additives,
   and
B) a filling comprising
   at least one biologically active compound and
   optionally, one or more auxiliaries.

It is decidedly surprising that the capsule preparations according to the invention are better suitable for applying biologically active compounds to plants than corresponding known preparations.

The capsule preparations according to the invention are distinguished by a series of advantages. Thus, the preparations contain the biologically active compounds in high concentrations, which means that the volume of the capsules can be minimized. Accordingly, their costs for transportation and storage are lower than those of conventional ampule preparations. Further, the capsule preparations according to the invention exceed the known ampule preparations with regard to various other effects. In the case of treating individual trees, for example, neither the cambium is destructed to a marked extent nor is the passage of water inhibited in the trees. The holes opened at the time of the application of the capsules are smaller than in the case of the conventional technique, and the openings of the holes are speedily covered. Hence, there is no need for covering the holes with wood chips etc. The active substances are enclosed in capsules, which guarantees that operators do not directly touch the active compounds at the time they are applied. Working with the capsule preparations is safe and does not bear any risks for the operators. There is also no need for recollecting empty containers, such as ampules, after the application.

A detailed description of the capsule preparations according to the invention and of the method of their use is given in the following.

The shell of the capsule preparations according to the invention comprises water-soluble polyoxyethylene having a number average molecular weight of 100,000 or more, at least one plasticizer and optionally, one or more additives.

Polyoxyethylene in the present context means a polyether having repeating units of the formula $-[CH_2-CH_2-O]-$. Preferred are water-soluble polyoxyethylenes having a number average molecular weight between 100,000 and 8,000,000, particularly preferred are such compounds of a number average molecular weight between 100,000 and 1,000,000. The polyoxyethylenes must be water-soluble, and it is desirable that they generally have a solubility of 5 g/l or more, particularly of 10 g/l or more in water at 20° C. These polyoxyethylenes can be used alone or in combination of two or more polyoxyethylenes having a different molecular weight in average to improve the water-solubility, the hardness, the elasticity, the lubricity, etc. of the capsule shell. The polyoxyethylenes are known or can be prepared by known processes, for instance by ring opening polymerization of ethyleneoxides.

Plasticizers in the present context are all customary compounds of this type, which are suitable to modify the rigidity of polyoxyethylenes and which are non-phyto-toxic. As examples of such plasticizers there may be mentioned polyethylene glycol having a molecular weight of 200 to 600, and surface-active agents containing a polyoxyethylene chain, such as polyoxyethylene sorbitan monolaurate, wherein the average molecular weight of the polyoxyethylene moiety is between 100 and 1000, and polyoxyethylene nonyl phenyl ether, wherein the average molecular weight of the polyoxyethylene moiety is between 400 and 1000.

These plasticizers can be present in the shell material in an amount of 1 to 20 parts by weight, preferably of 2 to 10 parts by weight per 100 parts by weight of the water-soluble polyoxyethylene.

The shell of the capsule preparations according to the invention can contain one or more additivies. Such compounds in the present context are selected from polymers, which are different from polyoxyethylenes, further selected from stabilizers, extenders, short fibers, colorants, surface-active agents and the like. Said components can be incorporated to adjust the hardness, the elasticity, the lubricity, the water-solubility, etc. of the shell material.

The polymers, which are different from polyoxyethylenes, include polymers which are customarily used for producing plastic-forming resins. Specific examples there of include for instance polyolefins such as polyethylene, polypropylene and polybutylene; vinyl polymers such as polyvinyl chloride (PVC), polyvinyl acetate, polyvinyl alcohol, polystyrene and polyacrylonitrile; polyacrylates and polymethacrylates; polyacetals; polycondensates and polyaddition products such as polyamides, polyesters, polyurethanes, polycarbonates and polyalkylene terephthalate; polyaryl ethers and polyimides; polyalkylene oxide alkyls and aikyl aryl ethers; polymeric polyalkylene oxides (provided that polyoxyethylene is excluded) such as homo- and co-polymers of propylene oxide; olefin/vinyl ester copolymers such as ethylenelvinyl acetate copolymers; ethylene/vinyl alcohol copolymers; olefin/acrylate and methacrylate copolymers such as ethylene/acrylic acid copolymers, ethylene/ethyl acrylate copolymers and ethylene/methyl-acrylate copolymers; ABS copolymers, styrene/acrylonitrile copolymers, styrene/butadiene copolymers; olefin/maleic anhydride copolymers such as ethylene/maleic anhydride copolymers; starches such as natural starch, amylose and starch/thermoplastic mixtures; sugar polymers such as polymaltose; celluloses and cellulose derivatives such as cellulose esters, cellulose ethers and cellulose nitrates; polyoxyalkylated celluloses and lignin sulfonates; hydrogels such as alginate; and natural resins such as colophony, gum arabic and agar-agar. These polymers can be present in an amount of up to 50 parts by weight, preferably up to 30 parts by weight per 100 parts by weight of the above-mentioned polyoxyethylene.

As examples of stabilizers, which can be present in the shell material of the capsule preparations according to the invention, there may be mentioned phenothiazine, thiourea, 1-acetyl-2-thiourea, etc. These stabilizers can be present in a concentration of about 1% by weight or less, preferably of about 0.5% by weight or less relative to the weight of the capsule shell.

Examples of extenders, which can be present in the shell material of the capsule preparations according to the invention, include calcium carbonate, talc, aluminum silicate, barytas, titanium dioxide, quartz sands, kaolins, carbon black and glass microbeads.

Furthermore, as examples of short fibers, which can be present in the shell material of the capsule preparations according to the invention, there may be mentioned inorganic fibers, such as glass fibers, and organic fibers, such as polyester fibers and polyamide fibers, said short fibers having a length of about 0.1 mm to about 1 mm.

As examples of colorants, which can be present in the shell material of the capsule preparations according to the invention, there may be mentioned organic or organic-based dye-stuffs or coloring pigments, such as iron oxide pigments, chrome oxide pigments and phthalocyanine.

The additives selected from extenders, short fibers and colorants can be present in the shell material of the capsule preparations according to the invention in an amount of 0 to 40 parts by weight, preferably of 0 to 20 parts by weight per 100 parts by weight of polyoxyethylene.

The capsule shell of the preparations according to the invention can be prepared by molding a mixture of abovementioned components for forming the capsule shell, either by using a customary molding method of therrrmoplastic resins (e.g. extrusion molding, injection molding, blow molding, vacuum forming) or by utilizing a molding technique for pharmaceutical capsule preparations.

The form of the shell of the capsule preparations according to the invention is not particularly limited. It can be selected from different types depending on the type of the plant to be treated, the application method (use of an implement) of the capsule preparations, the properties of the chemicals to be filled in, etc. For instance, the shells can have a cylindrical form one or both sides of which are hemispherically or conically closed, or can have a cylindrical form the corner of which is chamfered, or can have an ellipsoidal form, a spherical form, etc. Further, the capsule shell may be provided with projections on its surface to prevent the capsule preparation from being extruded by sap. The capsule shell may also be of a seal-type, such as an interlocking type or a seamless type, or in case where there is no possibility of moving of the biologically active substance to the outside of the capsule, the capsule shell may be of an open type the feed opening of which is left open.

The size of the capsule shell is not particularly limited, and usually preferred are those whose diameter is within the range of 4 to 10 mm, particularly of 6 to 9 mm, and whose length is within the range of 5 to 120 mm, particularly of 10 to 60 mm. Further, it is generally desirable that the thickness of the capsule shell is within the range of 20 to 400 $\mu$m, particularly of 100 to 300 $\mu$m.

The capsule preparations according to the invention comprise one or more biologically active compounds. These are to be understood as meaning all customary substances, which can be used for protecting plants, particularly trees, from damage and which have systemic properties. Further included are systematically active compounds which can be used for combating undesired vegetation, such as shrubs. As biologically active compounds, there may specifically be mentioned insecticidal compounds, fungicidal compounds, nematocidal compounds, herbicidal compounds, plant nutritive substances, plant growth regulants etc. Insecticidal and fungicidal compounds are preferred, insecticidal compounds are particularly preferred.

The following compounds may be mentioned as examples of insecticidal or nematocidal compounds, which can be present in the capsule preparations according to the invention:

O,O-dimethyl O-3-methyl-4-(methylsulfinyl)-phenylphosphorothioate, trans-1,4,5,6-tetrahydro-1-methyl-2-[2-(3-methyl-2-thienyl)-vinyl]-pyrimidine tartrate, (−)-(S)-2,3,5,6-tetrahydro-2-phenylimida[2,1-b]-thiazole hydrochloride, 1-(6-chloro-3-pyridylmethyl)-N-nitro-imidazolidin-2-ylideneamine, (RS)-S-sec-butyl O-ethyl 2-oxo-1,3-thiazolidin-3-yl-phosphorothioate, O-ethyl S,S-diisopropyl phosphorodithioate, N-[(6-chloro-3-pyridyl)-methyl]-N-cyano-N-methyl-acetamidine, N-[(6-chloro-3-pyridyl)-methyl]-N-ethyl-N-methyl-2-nitro-1,1-ethanediamine, N-(2-chloro-5-thiazolylmrethyl)-3-methyl-2-nitro-guanidine and 1-(2-chloro-5-thiazolylmethyl)-3,5-dimethyl-2-nitro-iminohexahydro-1,3,5-triazine, etc.

The following compounds may be mentioned as examples of fungicidal compounds, which can be present in the capsule preparations according to the invention:

Sulfenamides, such as dichlofluanid (Euparen®), tolylfluanid (Methyleuparen®), folpet and fluorofolpet;

benzimidazoles, such as carbendazim (MBC), benomyl, fuberidazole and thiabendazole or salts thereof;

thiocyanates, such as thiocyanatomethyl thiobenzothiazole (TCMTB) and methylene bisthiocyanate (MBT);

quaternary ammnonium compounds, such as benzyl dimethyltetradecylammonium chloride, benzyldimethyl dodecyl-ammonium chloride and dodecyl-dimethylammonium chloride;

morpholine derivatives, such as $C_{11}$–$C_{14}$-4-alkyl-2,6-dimethylmorpholine homologues (tridemorph), (+)-cis-4-[3-(4-t-butylphenyl)-2-methylpropyl]-2,6-dimethylmorpholine (fenpropimorf) and falimorph;

phenols, such as o-phenylphenol, tribromophenol, tetrachlorophenol, pentachlorophenol, 3-methyl-4-chlorophenol, dichlorophen and chlorophen or salts thereof;

azoles, such as triadimefon, triadimenol, bitertanol, tebuconazole, propiconazole, azaconazole, hexaconazole, prochloraz, cyproconazole, 1-(2-chloro-phenyl)-2-(1-chloro-cyclopropyl)-3-(1,2,4-triazol-1-yl)-propan-2-ol and 1-(2-chlorophenyl)-2-(1,2,4-triazol-1-yl-metbyl)-3,3-dimethyl-butan-2-ol;

iodopropargyl derivatives, such as iodopropargyl-butylcarbamate (IPBC) and iodo-propargyloxyethyl phenylcarbamate;

iodo derivatives, for example diiodomethyl-p-arylsulfones, such as diiodomethyl-p-tolyl-sulfone;

bromo derivatives, such as bromopol; isothiazolines, such as N-methylisothiazolin-3-one, 5-chloro-N-methylisothiazolin-3-one, 4,5-dichloro-N-octyl-isothiazolin-3-one, N-octylisothiazolin-3-one (octilinone), benzisothiazolinone and cyclopentene-isothiazoline;

pyridines, such as 1-hydroxy-2-pyridinethione and tetrachloro-4-methylsulfonylpyridine;

nitriles, such as 2,4,5,6-tetrachloroisophthalonitrile (chlorothalonil);

fungicides having an activated halogen group, such as Cl-Ac, MCA, tectamer, bromopol and promidox;

benzothiazoles, such as 2-mercaptobenzothiazole;

dicarboximides, such as iprodione, vinclozolin, procymidorie and dazomet; and quinolines, such as 8-hydroxyquinoline.

The following compounds may be mentioned as examples of herbicidal compounds, which can be present in the capsule preparations according to the inventon:

2-Methoxy-3,6-dichlorobenzoic acid methylamine, sodium 2-methoxy-3,6-dichlorobenzoate, potassium 4-amino-3,5,6-trichloro-2-pyridine carboxylate, chlorate, ammonium sulfamate, etc.

Such herbicidal compounds are suitable to control the growth of undesired plants, such as shrubs and bushes.

The following compounds may be mentioned as examples of plant nutritive substances, which can be present in the capsule preparations according to the invention:

Water-soluble metal compounds having a chlorophyll based structure, such as sodium chlorophyllin and sodium copper chlorophyllin;

water-soluble compounds which provide an element selected from the group consisting of iron, zinc and magnesium, including, as water-soluble iron compounds, ferrous chloride, ferrous nitrate, ferrous sulfate, ammonium ferrous sulfate, ferric acetate, ferric chloride, ferric nitrate, ferric sulfate, ferric citrate, ammonium iron citrate, iron glycerophosphate, ferric tartrate, ferric lactate, ferric glycolate, etc;

water-soluble magnesium compounds and water-soluble zinc compounds which correspond to these water-soluble iron compounds; and fernrc-zinc double salts, ferric-manganese double salts, or zinc-manganese double salts, etc. of citrate and sulfate.

The capsule preparations according to the invention can contain one biologically active compound or combinations of two or more of such compounds.

The capsule preparations according to the invention can contain the biologically active compounds as such or in admixture with one or more agriculturally acceptable auxiliaries, such as carriers, extenders, stabilizers, surface-active agents and colorants.

The following compounds may be mentioned as examples of carriers and extenders, which can be contained in the filling material of the capsule preparations according to the invention.

Ground natural minerals, such as kaolins, clays, talc, chalk, quartz, attapulgite, montmorillonite or diatomaceous earth; ground synthetic minerals, such as highly-dispersed silicic acid, alumina and silicates; crushed and fractionated natural rocks such as calcite, marble, pumice, sepiolite and dolomite; as well as organic substances such as various starches, celluloses and processed products thereof, saccharides and synthetic polymers.

The capsule preparations according to the invention can contain any customary types of anionic, cationic, non-ionic or amphoteric surface-active agents in the filling material. Preferred are anionic, non-ionic as well as cationic surface-active agents.

The following substances may be mentioned as examples of anionic surface-active agents:

Sodium, calcium or ammonium salts of alkyl-sulfate, sodium, calcium or ammonium salts of polyoxy-ethylene-alkyl ether sulfate, sodium, calcium or ammonium salts of polyoxyethylenebenzyl (or styryl)phenyl ther sulfate, sodium, calcium or ammonium salts of polyoxyethblene-polyoxypropylene block polymer sulfate, sodium, calcium, ammonium or alkanolamine salts of alkcylsulfonate, sodium, calcium, ammonium or alkanolamine salts of dialkylsulfosuccinate, sodium, calcium, ammonium or alkanolamine salts of alkylbenzenesulfonate, sodium, calcium, ammonium or alkanolamine salts of mono- or di-alkyl-naphthalenesulfonate, sodium, calcium, ammonium or alkanolamine salts of naphthalene sulfonate form aldehyde condensate, sodium, calcium, ammonium or alkanolamine salts of lignin sulfonate, sodium, calcium, ammonium or alkanolamine salts of polyoxyethylenealkylphenyl ether sulfonate, sodium, calcium, ammonium or alkanolamine salts of polyoxyethylenealkyl ether sulfosuccinate, sodium or calcium salts of polyoxyethylene-alkyl ether phosphate, sodium or calcium salts of mono- or di-alkylphenyl ether phosphate, sodium or calcium salts of polyoxyethylene-benzyl (or styryl) phenyl ether phosphate, sodium or calcium salts of polyoxyethylene-polyoxypropylene block polymer phosphate, etc.

The following substances may be mentioned as examples of non-ionic surface-active agents:

Polyoxyethylene alkyl ether, polyoxyethylene alkyl phenyl ether, polyoxyethylene alkyl phenyl ether formaldehyde condensate, polyoxyethylene-polyoxyethylene block polymer, polyoxyethylene-polyoxyethylene block polymer alkyl phenyl ether, sorbitan fatty acid ester, polyoxyethylene fatty acid ester, polyoxyethylene sorbitan fatty acid ester, and polyoxyethylene castor oil ether.

The following substances may be mentioned as examples of colorants, which can be contained in the filling material of the capsule preparations according to the invention:

Inorganic pigments, for example iron oxide, titanium oxide and Prussian Blue, and organic dyestuffs, such as alizarin dyestuffs, azo dyestuffs and metal phthalocyanine dyestuffs.

Further, the filling material of the capsule preparations according to the invention can contain as stabilizers any customary substances, which are suitable to stabilize the biologically active compounds or formulations thereof.

The concentrations of biologically active compounds in the filling material can be varied within a wide range. The concentrations are generally from 0.1 to 100% by weight, preferably from 5 to 100% by weight.

The concentrations of the auxiliaries in the filling material can also be varied within a relatively wide range. In detail, the ranges are as follows:

carriers and/or extenders:
generally 0–90% by weight,
preferably 0–50% by weight, stabilizers and/or colorants:
generally 0–10% by weight,
preferably 0–5% by weight, surface-active agents:
generally 0–20% by weight,
preferably 0–10% by weight.

The biological active compounds or their mixtures with auxiliaries can be filled into the capsule shells in known manner. For instance, when using solid biologically active substances, they can directly be filled into the capsule shells in the form of powders or granules as such, or after having been heated and melted, or they can be filled into the capsule shells in the form of powders or granules comprising the active compounds in admixture with carriers, extenders, stabilizers, surface-active agents etc. When using liquid biologically active compounds, they can be filled into the capsule shells in the form of powders or granules, which can be obtained by impregnating the liquid compounds with solid carriers optionally followed by the addition of extenders, stabilizer, surface-active agents etc. When liquid biologically active compounds are used, which do not dissolve the capsule shell, said compounds can directly be filled into the capsule shells before sealing them.

The capsule preparations according to the invention produced as mentioned above, are very advantageous for treating plants, such as trees and shrubs, with chemicals.

The capsule preparations according to the invention can be applied, for instance, by boring a hole into the trunk or branch of a tree with a drill, etc. and by inserting the capsule preparation into the hole. After inserting the capsule preparation, the opening of the hole may be covered by wood chips, etc. However, even if the hole remains as it is without covering, the opening is gradually covered by sap, and finally cambia are swollen (i.e. calluses are formed), thus making the opening completely covered.

If a capsule preparation according to the invention is inserted into the trunk of a tree, polyoxyethylene, i.e. a material of the capsule shell, is gradually dissolved, whereby the biologically active substance is released outside the capsule and accordingly absorbed by the tree. The biologically active substance thus absorbed moves throughout the tree to thereby exhibit its activity.

The type of trees which can be treated by the capsule preparations according to the invention is not particularly restricted. Examples thereof include pine trees, such as Japanese red pine, Japanese black pine, silver fir, fir, Japanese larch and Norway spruce; beech trees, such as Japanese beech, Japanese chestnut, Castanopsis and Japanese oak; and cedar trees, such as Japanese cedar, sawara cypress and Japanese cypress.

Depending on the biologically active compounds in the formulations, the capsule preparations according to the invention can be used for various purposes. The preparations can preferably employed to combat parasitic pests, such as insects or nematodes, or for the control of microbicidal diseases, such as infections by molds, fungi, bacteriae etc. on plants, such as trees.

As examples of insects to be combated, there may be mentioned Coleptera insects such as Cerambycidae, Scolytidae, Curculionidae, Scarabaeidae and Chrysomelide; Hymenoptera insects such as Cynipidae and Tenthredinidae; Diptera insects such as Cecidomyiidae; Hemiprera insects such as Aphididae, Psyllidae, Hemiptera, Ricaniidae, Aphrophoridae and Pentatomidae; Lepidoptera insects such as hairy caterpillar, Fumea, Merpho, coalin moth, Tortricidae, Sesiidae, Cossidae and Hepialidae; *Bursaphelenchus xylophilus* Nickle.

Furthermore, as examples of molds, fungi and bacteriae to be combated, there may be mentioned various, plant disease causative microorganisms, such as Plasmodiophoromycetes, Oomycetes, Chytridiomycetes, Zygomycetes, Ascomycetes, Basidiomycetes and Deuteromycetes; various, plant disease causative microorganisms, such as Pseudomonadaceae, Rhizobiaceae, Enterobacteriaceae, Corynebacteriaceae and Streptomycetaceae; and others.

For combating parasitic pests or microbicidal diseases on plants, such as trees, the amount of capsule preparation applied can be varied depending on the size of the plant, the type and the content of the biologically active compound, the degree of infestation by parasitic pests and/or by microorganisms. The specific amount applied can be adjusted by changing the number of capsule preparations administered. In the case where a plurality of capsule preparations is administerd, it is preferred to bore holes spaced at appropriate intervals for administration.

The invention can be illustrated by the following Examples, but the invention is in no way restricted to these Examples. The active compounds used in Examples are shown below.

The following biologically active compounds were used in the Examples described below:

Compound A:
O,O-dimethyl O-3-methyl-4-(methylsulfinyl)-phenylpbosphorothioate,

Compound B:
trans-1,4,5,6-tetrahydro-1-methyl-2-[2-(3-methyl-2-thienyl)-vinyl]-pyrimidinetartrate, Compound C:
(−)-(S)-2,3,5,6-tetrahydro-6-phenyl-imida[2,1-b]thiazole hydrochloride, Compound D:
1-(6-chloro-3-pyridylmethy)-N-nitro-imidazolidin-2-ylideneamine.

EXAMPLES FOR THE PRODUCTION OF CAPSULE SHELLS

Example I

Ten parts by weight of polyoxyethylene glycol having a number average molecular weight of 400 were added to 90 parts by weight of polyoxyethylene having a number average molecular weight of 100,000. The resulting mixture was then subjected to injection molding to thereby obtain small test-tube like capsule shells having an external diameter of 7.2 mm, an internal diameter of 6.7 mm and a length of 30 mm.

Example II

Ten parts by weight of polyethylene glycol having a number average molecular weight of 6,000 and 10 parts by weight of polyethylene glycol having a number average molecular weight of 400 were added to 80 parts by weight of polyoxyethylene having a number average molecular weight of 100,000. The resulting mixture was then subjected to injection molding to thereby obtain small test-tube like capsule shells having an external diameter of 7.2 mm, an internal diameter of 6.7 mm and a length of 30 mm.

Example III

Ten parts by weight of polyethylene glycol having a number average molecular weight of 400 were added to 70 parts by weight of polyoxyethylene having a number average molecular weight of 100,000 and 20 parts by weight of polyoxyethylene having a number average molecular weight of 8,000,000. The resulting mixture was then subjected to injection molding to thereby obtain small test-tube like capsule shells having an external diameter of 7.2 mm, an internal diameter of 6.7 mm and a length of 30 mm.

PREPERATION EXAMPLES

Example 1

1.4 g of the heated and melted Compound A were filled into a capsule shell which was obtained according to Example I. The capsule preparation was then left at room temperature to allow crystallization of Compound A.

Example 2

1.4 g of the heated and melted Compound A were filled into a capsule shell which was obtained according to Example II. The capsule preparation was then left at room temperature to allow crystallization of Compound A.

Example 3

Five parts by weight of a highly water-absorbable acrylate-type polymer in powdered form were mixed with 95 parts by weight of the heated and melted Compound A. 1.4 g of this mixture, in its melted state, were filled into a capsule shell which was obtained according to Example I. The capsule preparation was then left at room temperature to allow crystallization of the melt.

Example 4

Fifty parts by weight of Compound D were mixed with 50 parts by weight of heated and melted polyethylene glycol having a number average molecular weight of 4,000. While melted, 1.4 g of this mixture were filled into a capsule shell which was obtained according to Example I. The capsule preparation was then left at room temperature to allow solidification of the melt.

Example 5

Thirty parts by weight of Compound B were mixed with 70 parts by weight of heated and melted polyethylene glycol having a number average molecular weight of 4,000. While melted, 1.4 g of this mixture were filled into a capsule shell which was obtained according to Example I. The capsule preparation was then left at room temperature to allow solidification of the melt.

Example 6

Thirty parts by weight of Compound C were mixed with 70 parts by weight of heated and melted polyethylene glycol having a number average molecular weight of 4,000. While melted, 1.4 g of this mixture were filled into a capsule shell which was obtained according to Example I. The capsule preparation was then left at room temperature to allow solidification of the melt.

BIOLOGICAL TEST

Example A

Test for preventing pines from diseases.

Holes having a diameter of 7.5 mm each were bored to 15 years-old Japanese black pines at breast height with a motorized drill early in the summer (at the beginning of June). The holes were spaced at equal intervals around the trunks of the trees. Capsule preparations of one of Examples 1, 5 or 6 were inserted into each of the holes. One day after the chemical treatment, the holes started to cover and half a year later, they were completely covered by the calluses formed. Thirty days after the chemical treatment, three holes (diameter: 4 mm; depth: 10 mm) were made at the total of 3 points in each tree (2 points in the upper part of the main branch; and 1 point in the main trunk). Then, approximately 15000 *Bursaphelenchus xylophilus* Nickle were inoculated per hole. Two months after the inoculation, the state of resin of the pines was examined by criteria to judge resin (by Oda method). For the test, 5 pines were used per experimental plot and the results were shown in average. In this test, neither water passage inhibition nor phytotoxicity such as cambium destruction of trees were observed. The results are shown in the following Table A.

TABLE A

| Experimental plot Preparation used | Number of trees treated with chemicals | Chemical dosage (g.a.i./tree) | Effect |
|---|---|---|---|
| Example 1 | 6 | 8.4 | +++ |
| Example 5 | 6 | 2.5 | +++ |
| Example 6 | 6 | 2.5 | +++ |

The criteria to judge resin of a clump of pines are shown in the following Table B.

TABLE B

Criteria to judge resin of a clump of pines (by Oda method)

| Normal | | | Abnormal | |
|---|---|---|---|---|
| +++ | ++ | + | − | ○ |
| Resin accumulates and flows down as the time passed | Resin seems to be slightly smaller than that of (+++) | particles partically appeared | Resinous zones with a few fine particles | Sort of drying; not resinous |

We claim:

1. A method for administering a biologically active compound to a plant, said method comprising inserting into said plant a capsule preparation alone comprising:
   A) a capsule shell consisting essentially of:
      i) water-soluble polyoxyethylene having an average molecular weight between 100,000 and 8,000,000;
      ii) at least one plasticizer; and
      iii) optionally, one or more additives;
      and
   B) a filling comprising:
      i) at least one insecticidal or nematocidal compound selected from the group consisting of:
         a) O,O-dimethyl O-3-methyl-4-(methylsulfinyl) phenylphosphorothioate,
         b) trans-1,4,5,6-tetrahydro-1-methyl-2-[2-(3-methyl-2-thienyl)-vinyl]-pyrimidine tartrate,
         c) (−)-(S) -2,3,5,6-tetrahydro-2-phenylimida[2,1-b] thiazole hydrochloride,
         d) 1-(6-chloro-3-pyridylmmethyl)-N-nitro-imidazolidin-2-ylideneamine,
         e) (RS)-S-sec-butyl O-ethyl 2oxo-1,3-thlazolidin-3-yl-phosphorothioate,
         f) O-ethyl S,S-diisopropyl phosphorodithioate,
         g) N-[(6-chloro-3-pyridyl)-methyl]-N-cyano-N-methyl acetamidine,
         h) N-[(6-chloro-3-pyridyl)-methyl]-N-ethyl-N-methyl-2-nitro-1,1-ethanediamine,
         i) N-(2-chloro-5-thiazolylmethyl)-3-methyl-2-nitro-guanidine; and
         j) 1-(2-chloro-5-thiazolylmethyl)-3,5-dimethyl-2-nitro-iminohexahydro-1,3,5-triazine; and
      ii) optionally, one or more auxiliaries.

2. A method according to claim 1, wherein the capsule preparation is inserted into a hole in the plant.

3. A method for administering a biologically active compound to a plant, said method comprising inserting into said plant a capsule preparation alone comprising:
   A) a capsule shell consisting of
      i) water-soluble polyoxyethylene having an average molecular weight between 100,000 and 8,000,000;
      ii) at least one plasticizer; and
      iii) optionally, one or more additives;
      and
   B) a filling comprising:
      i) at least one insecticidal or nematocidal compound selected from the group consisting of:
         a) O,O-dimethyl O-3-methyl-4-(methylsulfinyl) phenylphosphorothioate,
         b) trans-1,4,5,6-tetrahydro-1-methyl-2-[2-(3-methyl-2-thienyl)vinyl]-pyrimidine tartrate,
         c) (−)-(S)-2,3,5,6-tetrahydro-2-phenylimida[2,1-b] thiazole hydrochloride,
         d) 1-(6-chloro-3-pyridylmmethyl)-N-nitro-imidazolidin-2-ylideneamine,
         e) (RS)-S-sec-butyl O-ethyl 2-oxo-1,3-thiazolidin-3-yl-phosphorothioate,
         f) O-ethyl S,S-diisopropyl phosphorodithioate,
         g) N-[(6-chloro-3-pyridyl)-methyl]-N-cyano-N-methyl-acetamidine,
         h) N-[(6-chloro-3-pyridyl)-methyl]-N-ethyl-N-methyl-2-nitro-1,1-ethanediamine,
         i) N-(2-chloro-5-thiazolylmethyl)-3-methyl-2-nitro-guanidine; and
         j) 1-(2-chloro-5-thiazolylmethyl)-3,5-dimlathyl-2-nitro-iminohexahydro-1,3,5-triazine; and
      ii) optionally, one or more auxiliaries.

* * * * *